(12) United States Patent
Back et al.

(10) Patent No.: US 10,577,310 B2
(45) Date of Patent: Mar. 3, 2020

(54) PROCESS FOR SYNTHESIZING AN AMIDO ALKYL BETAINE STARTING FROM AN ALCOHOL, AN AMIDO ALKYL BETAINE PREPARED BY THE PROCESS WITH INCREASED VISCOSITY, AND USE THEREOF AS A VISCOELASTIC SURFACTANT

(71) Applicant: RHODIA OPERATIONS, Paris (FR)

(72) Inventors: Olivier Back, Lyons (FR); Pascal Herve, Talence (FR); Philippe Marion, Vernaison (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 16/091,205

(22) PCT Filed: Apr. 4, 2017

(86) PCT No.: PCT/EP2017/058041
§ 371 (c)(1),
(2) Date: Oct. 4, 2018

(87) PCT Pub. No.: WO2017/174616
PCT Pub. Date: Oct. 12, 2017

(65) Prior Publication Data
US 2019/0127316 A1    May 2, 2019

(30) Foreign Application Priority Data

Apr. 8, 2016 (EP) .................................. 16305420

(51) Int. Cl.
| | | |
|---|---|---|
| C07C 235/10 | (2006.01) | |
| C07C 67/22 | (2006.01) | |
| C07C 231/02 | (2006.01) | |
| A61K 8/44 | (2006.01) | |
| C07C 231/12 | (2006.01) | |
| C07C 253/30 | (2006.01) | |
| C07C 67/31 | (2006.01) | |
| C07C 67/03 | (2006.01) | |
| A61Q 19/00 | (2006.01) | |
| C07C 67/08 | (2006.01) | |
| C07C 67/293 | (2006.01) | |
| C09K 8/584 | (2006.01) | |

(52) U.S. Cl.
CPC ............ *C07C 235/10* (2013.01); *A61K 8/442* (2013.01); *A61Q 19/00* (2013.01); *C07C 67/03* (2013.01); *C07C 67/08* (2013.01); *C07C 67/22* (2013.01); *C07C 67/293* (2013.01); *C07C 67/31* (2013.01); *C07C 231/02* (2013.01); *C07C 231/12* (2013.01); *C07C 253/30* (2013.01); *A61K 2800/10* (2013.01); *A61K 2800/48* (2013.01); *C09K 8/584* (2013.01)

(58) Field of Classification Search
CPC ... C07C 69/734; C07C 235/10; C07C 231/02; C07C 231/12; C07C 253/30; C07C 67/03; C07C 67/08; C07C 67/22; C07C 67/31; C07C 67/293; C07C 255/13; A61K 2800/10; A61K 2800/48; A61K 8/442; A61K 2800/00; A61Q 19/00; C09K 8/584
See application file for complete search history.

(56) References Cited

U.S. PATENT DOCUMENTS

| | | | |
|---|---|---|---|
| 4,237,067 A | | 12/1980 | Kuster et al. |
| 2003/0162952 A1 | | 8/2003 | Keck et al. |

FOREIGN PATENT DOCUMENTS

| | | | |
|---|---|---|---|
| EP | 1338644 A1 | | 8/2003 |
| JP | 05043530 | * | 2/1993 |
| JP | 9095474 A2 | | 4/1997 |
| JP | 4089461 A2 | | 3/1998 |
| WO | 9856497 A1 | | 12/1998 |

OTHER PUBLICATIONS

JP05043530 machine translation (Year: 1993).*
Genxing, S. et al., "Preparation and Application of Fattyamidopropyl Betaine Amphoteric Fatliquor", College of Resource and Environment, Shaanxi University of Science and Technology, College of Material Science and Chemical Engineering, Tianjin University of Science and Technology, China Leather, 2007, vol. 36, No. 19, pp. 41-44. English Language abstract included.
Gravesholt, S., "Viscoelasticity in Highly Dilute Aqueous Solutions of Pure Cationic Detergents", Journal of Colloid and Interface Science, Dec. 1976, vol. 57, No. 3, pp. 575-577.
Hoffmann, et al., "Influence of Ionic Surfactants on the Viscoelastic Properties of Zwitterionic Surfactant Solutions", Langmuir 1992, vol. 8, No. 9, pp. 2140-2146.
Hoffmann, et al., "The rheological behaviour of different viscoelastic surfactant solutions", Tenside Surfactants Detergents, 1994, vol. 31, No. 6, pp. 389-400.

* cited by examiner

*Primary Examiner* — Yevgeny Valenrod
*Assistant Examiner* — Blaine G Doletski (57) ABSTRACT

The present invention relates to a new process for synthesizing an amido alkyl betaine starting from a linear alcohol having from 8 to 22 carbon atoms, to an amido alkyl betaine prepared by the process with increased viscosity in water, and also to use thereof as a viscoelastic surfactant in oil and gas applications and home personal care applications. The present invention also relates to a process for synthesizing an amido amine starting from a linear alcohol having from 8 to 22 carbon atoms, and to an amido amine prepared by the process.

15 Claims, 7 Drawing Sheets

PROCESS FOR SYNTHESIZING AN AMIDO ALKYL BETAINE STARTING FROM AN ALCOHOL, AN AMIDO ALKYL BETAINE PREPARED BY THE PROCESS WITH INCREASED VISCOSITY, AND USE THEREOF AS A VISCOELASTIC SURFACTANT

This application is a U.S. national stage entry under 35 U.S.C. § 371 of International Application No. PCT/EP2017/058041 filed Apr. 4, 2017, which claims priority to European application No. 16305420.8 filed on Apr. 8, 2016. The entire contents of these applications are explicitly incorporated herein by this reference.

TECHNICAL FIELD

The present invention relates to a new process for synthesizing an amido alkyl betaine starting from a linear alcohol having from 8 to 22 carbon atoms, to an amido alkyl betaine prepared by the process with increased viscosity in water, and also to use thereof as a viscoelastic surfactant. The present invention also relates to a process for synthesizing an amido amine starting from a linear alcohol having from 8 to 22 carbon atoms, and to an amido amine prepared by the process.

BACKGROUND OF THE INVENTION

The property of viscoelasticity is generally well known in the field, and reference can be made to S. Gravsholt, Journal of Coll. And Interface Sci., 57(3), 575(1976); Hoffmann et al., "*Influence of Ionic Surfactants on the Viscoelastic Properties of Zwitterionic Surfactant Solutions,*" Langmuir, 8, 2140-2146 (1992); and Hoffmann et al., "*The Rheological Behaviour of Different Viscoelastic Surfactant Solutions,*" Tenside Surf. Det., 31, 389-400 (1994).

A betaine is any neutral compound carrying separated charges where a positively charged atom, such as a quaternary ammonium or a phosphonium group, is not adjacent to a negatively charged atom, such as carboxylate group. That is, a betaine is a chemical compound that carries a total net charge of zero and is thus electrically neutral, but carries formal charges on different atoms. Notably, it is well known in the field that long chain amido alkyl betaines are effective as viscoelastic surfactants.

Viscoelastic surfactants have continued to grow their role in oil & gas applications and home personal care applications, and the related markets are also expected to continue to show important growth, because of their various advantages over alternative solutions based on polymers. However, such a growth has been inhibited by high cost and low availability of raw materials which are required to produce viscoelastic surfactants.

Among the various fatty acids that can be used as raw materials for the preparation of long chain amido alkyl betaines, erucic acid is often employed in the aforementioned applications because of the high level of viscosity performance at high temperatures attainable by the betaine derived therefrom. For instance, WO 98/56497 (Rhodia Inc.), published on Dec. 17, 1998, discloses viscoelastic surfactants derived from erucic acid. However, erucic acid is a rather expensive raw material with limited availability.

Accordingly, it is required to find alternative viscoelastic surfactants which can be produced in a cost effective manner. That is, there exists a need for an alternative sourcing of raw materials for the synthesis of a long chain amido alkyl betaine and a commercially applicable process for synthesizing the same.

BRIEF DESCRIPTION OF FIGURES

In FIG. 7, (a) refers to 1.5 wt % of commercially available betaine made from oleic acid (Mirataine® BET O-30), (b) refers to 1.3 wt % of alkoxy betaine prepared from Example 8 using oleyl alcohol (85%), and (c) refers to 1.5 wt % of alkoxy betaine prepared from Example 9 using oleyl alcohol (60%).

DESCRIPTION OF THE INVENTION

The object of the present invention is hence to provide a process for synthesizing a long chain amido alkyl betaine, which maintains a high level of viscosity performance at high temperatures, in a cost effective manner.

The present invention therefore relates to a process for synthesizing an amido alkyl betaine from a linear alcohol having from 8 to 22 carbon atoms, characterized in that a) in a first step, a linear alcohol having from 8 to 22 carbon atoms is condensed with an acrylonitrile to produce a β-alkoxy nitrile;

b) in a second step, the β-alkoxy nitrile obtained from step a) is reacted with a short chain alcohol having from 1 to 4 carbon atoms to produce a β-alkoxy alkyl ester;

c) in a third step, said β-alkoxy alkyl ester is reacted with an amino alkyl amine to produce an amido amine; and d) in a fourth step, said amido amine is reacted with an alkylating agent to produce an amido alkyl betaine.

The present invention further relates to a process for synthesizing an amido alkyl betaine from a linear alcohol having from 8 to 22 carbon atoms, characterized in that a) in a first step, a linear alcohol having from 8 to 22 carbon atoms is condensed with an alkyl acrylate to produce a β-alkoxy ester;

b) in a second step, the β-alkoxy ester obtained from step a) is reacted with a short chain alcohol having from 1 to 4 carbon atoms to produce a β-alkoxy alkyl ester;

c) in a third step, said β-alkoxy alkyl ester is reacted with an amino alkyl amine to produce an amido amine; and d) in a fourth step, said amido amine is reacted with an alkylating agent to produce an amido alkyl betaine.

Preferred embodiments of the process in accordance with the present invention are set forth in the dependent claims and the detailed description hereinafter.

In addition, the present invention relates to an amido alkyl betaine and an amido amine obtainable from the process, to use of the amido alkyl betaine as a viscoelastic surfactant in oil and gas applications and home personal care applications. The present invention further relates to a mixture of amido alkyl betaines obtainable from the process using a mixture of linear alcohols having from 8 to 22 carbon atoms.

In the first step a) of the process according to the present invention, an acrylonitrile or an alkyl acrylate is added to a linear alcohol having from 8 to 22 carbon atoms for a duration of from 0.5 to 4.0 hours at a temperature of from 10° C. to 80° C., preferably 1.0 to 3.0 hours at a temperature of from 15° C. to 60° C., more preferably 1.5 to 2.5 hours at a temperature of from 20° C. to 40° C.

In step a), an acrylonitrile or an alkyl acrylate is added in an equivalent from 0.8 to 2.0, preferably in an equivalent from 0.9 to 1.5, with respect to the linear alcohol having from 8 to 22 carbon atoms.

In the present invention, the term "a linear alcohol having from 8 to 22 carbon atoms" is intended to denote an alcohol with a long aliphatic chain having from 8 to 22 carbon atoms, which may be either saturated or unsaturated. Such an alcohol is also known as a fatty alcohol, which is usually derived from naturally occurring fatty acid. Examples of the linear alcohol having from 8 to 22 carbon atoms suitable for being used in the present invention comprise, but are not limited to, 1-octanol (capryl alcohol), 1-decanol (capric alcohol), 1-dodecanol (lauryl alcohol), 1-tetradecanol (myristal alcohol), 1-hexadecanol (cetyl alcohol), 1-octadecanol (stearyl alcohol), oleyl alcohol ((Z)-octadec-9-en-1-ol), 1-icosanol (arachidyl alcohol), erucyl alcohol ((Z)-docos-13-en-1-ol), 1-docosanol (behenyl alcohol), or mixtures thereof.

In accordance with a particularly preferred embodiment of the process of the present invention, oleyl alcohol is used as a linear alcohol having from 8 to 22 carbon atoms, because oleyl alcohol is relatively cheap and has abundant availability.

In case an acrylonitrile is used as the starting material in step a), a linear alcohol having from 8 to 22 carbon atoms is condensed with an acrylonitrile to produce a β-alkoxy nitrile as an intermediate through a base catalyzed conjugate addition.

In case an alkyl acrylate is used as a starting material in step a), a linear alcohol having from 8 to 22 carbon atoms is condensed with an alkyl acrylate to produce a β-alkoxy ester as an intermediate through a base catalyzed conjugate addition.

Conjugate addition refers to a 1,4-addition of a nucleophile to an activated olefin such as a α,β-unsaturated carbonyl compound or α,β-unsaturated nitrile compound. Specific examples of a base catalyst which can be used in conjugate addition include, but are not limited to, sodium hydroxide, potassium hydroxide, sodium methoxide, 1,4-diazabicyclo[2.2.2]octane (DABCO; $N_2(C_2H_4)_3$), triethylamine (TEA), sodium carbonate ($Na_2CO_3$), pyridine ($C_5H_5N$), sodium bicarbonate ($NaHCO_3$), potassium carbonate ($K_2CO_3$), sodium hydride, sodium ethoxide, and potassium tert-butoxide.

In accordance with a particularly preferred embodiment of the process of the present invention, potassium tert-butoxide is used as a base catalyst in step a).

Examples of an alkyl acrylate which can be used in step a) of the present invention include, but are not limited to, methyl acrylate, ethyl acrylate, propyl acrylate, iso-propyl acrylate, butyl acrylate, iso-butyl acrylate, tert-butyl acrylate, hexyl acrylate, octyl acrylate, iso-octyl acrylate, decyl acrylate, iso-decyl acrylate, 2-ethylhexyl acrylate, and 2-propylheptyl acrylate. Particularly preferred alkyl acrylates are iso-propyl acrylate, butyl acrylate, and tert-butyl acrylate, among which tert-butyl acrylate is particularly preferred.

In the second step b) of the process in accordance with the present invention, a β-alkoxy nitrile or a β-alkoxy ester obtained from step a) is reacted with a short chain alcohol having 1 to 4 carbon atoms to produce a β-alkoxy alkyl ester at a temperature of from 50 to 250° C. for a duration of from 0.5 to 72.0 hours, preferably from 60 to 150° C. for a duration of from 6.0 to 72.0 hours.

In case a β-alkoxy nitrile obtained from step a) is used, the corresponding β-alkoxy alkyl ester is produced in step b) through an initial Pinner reaction, which refers to a reaction of a nitrile with an alcohol and an acid, for instance hydrochloric acid and sulphuric acid. The initial reaction product of a Pinner reaction is an iminoether salt, which is also known as a Pinner salt. In the presence of water, this salt forms an ester. In this case, an excess of acid, preferably from 2 to 10 equivalents is required.

When step b) reaction is completed, the obtained mixture is cooled to around 0° C. and neutralized using an aqueous solution of a base (for instance, NaOH) so that its pH should become 3 or more, and is subsequently extracted, dried over $MgSO_4$, filtered and evaporated so as to afford the corresponding β-alkoxy alkyl ester.

In case a β-alkoxy ester obtained from step a) is used, the corresponding β-alkoxy alkyl ester is produced in step b) through an acid-catalysed transesterification. In this case, a catalytic quantity of acid is sufficient to promote the reaction, preferably from 0.01 mol % to 60 mol % with respect to the β-alkoxy ester.

Examples of a short chain alcohol having 1 to 4 carbon atoms which can be used in the second step b) include, but are not limited to, methyl alcohol, ethyl alcohol, propyl alcohol, and butyl alcohol. Particularly preferred short chain alcohols having 1 to 4 carbon atoms to be used in the second step b) are methyl alcohol and ethyl alcohol.

When acid-catalysed transesterification is completed, the obtained mixture is neutralized using an aqueous solution of a base (for instance, NaOH) in a suitable reactor, preferably under mechanical stirring and is subsequently extracted, dried over $MgSO_4$, filtered and evaporated so as to afford the corresponding β-alkoxy alkyl ester.

In the third step c) of the process in accordance with the present invention, a β-alkoxy alkyl ester obtained from step b) is reacted with an amino alkyl amine to produce an amido amine at a temperature of from 90 to 150° C. for a duration of from 0.5 to 24.0 hours under an inert atmosphere.

In a round bottom flask, a β-alkoxy alkyl ester obtained from step b) and then an amino alkyl amine are mixed, to which sodium methoxide solution in 25 wt % methanol is added as a catalyst. Methanol which is formed during the reaction should be distilled off over the course of the reaction and the excess of the amino alkyl amine is then distilled under vacuum. The crude product is then purified using standard techniques such as distillation or flash chromatography. After evaporation, the corresponding amido amine is obtained as a pale yellow oil.

Examples of an amino alkyl amine include, but are not limited to, 1,2-diaminoethane, 1,2-diaminopropane, 1,3-diaminopropane, and N-substituted diaminopropane such as 1-amino-3-methylaminopropane, 3-diethylaminopropylamine (DEAPA), and dimethylaminopropylamine (DMAPA).

In accordance with a preferred embodiment of the process of the present invention, N-substituted diaminopropane is used as an amino alkyl amine in step c).

In accordance with a particularly preferred embodiment of the process of the present invention, DMAPA is used as an amino alkyl amine in step c).

In the fourth step d) of the process in accordance with the present invention, an amido amine obtained from step c) is reacted with an alkylating agent to produce an amido alkyl betaine at a temperature of from 60 to 90° C. for a duration of from 0.5 to 24.0 hours under an inert atmosphere.

In step d), an alkylating agent is added in an equivalent from 1.0 to 2.0, preferably in an equivalent from 0.6 to 1.5, more preferably in an equivalent from 0.8 to 1.3 with respect to the amido amine.

In a round bottom flask equipped with a mechanical stirring, an amido amine obtained from step c) is dissolved in a suitable solvent, for instance a water:iso-propanol (60:40) mixture. An alkylating agent is then added to the mixture, which is stirred continuously until there remains no free amido amine. The corresponding amido alkyl betaine is obtained as a pale yellow viscous solution.

In a preferred embodiment of the present invention, it is required to add additional amount of alkylating agent so as to achieve full conversion of an amido amine to an amido alkyl betaine.

Examples of an alkylating agent include, but are not limited to, sodium 3-chloro-2-hydroxy-1-propanesulfonate and sodium monochloroacetate (SMCA).

In accordance with a preferred embodiment of the process of the present invention, SMCA is used as an alkylating agent in step d).

Another aspect of the present invention relates to an amido alkyl betaine of the following general chemical formula (1), which can be prepared by the process of the present invention:

(1)

wherein the amino alkyl amine reagent used in step c) is DMAPA and R is a saturated or unsaturated linear hydrocarbon radical having from 8 to 22 atoms.

Further aspect of the present invention relates to a use of the amido alkyl betaine obtainable by the process of the present invention as a viscoelastic surfactant in oil and gas applications such as viscoelastic stimulation fluid or sand packing fluid, and in home personal care applications. The amido alkyl betaine according to the present invention may be used as a raw material, for example, for the preparation of rinse-off home personal care products like body wash or shampoos, and also for the preparation of industrial cleaning solutions or agricultural active formulations.

The present invention further relates to a process for synthesizing an amido amine from a linear alcohol having from 8 to 22 carbon atoms, characterized in that a) in a first step, a linear alcohol having from 8 to 22 carbon atoms is condensed with an acrylonitrile or an alkyl acrylate to produce a β-alkoxy nitrile or a β-alkoxy ester respectively;

b) in a second step, the β-alkoxy nitrile or β-alkoxy ester obtained from step a) is reacted with a short chain alcohol having 1 to 4 carbon atoms to produce a β-alkoxy alkyl ester; and c) in a third step, said β-alkoxy alkyl ester is reacted with DMAPA to produce an amido amine, wherein in step a), an acrylonitrile or an alkyl acrylate is added in an equivalent from 1.0 to 2.0 with respect to the linear alcohol having from 8 to 22 carbon atoms.

What has been said above for a process for synthesizing an amido alkyl betaine from a linear alcohol having from 8 to 22 carbon atoms in accordance with the present invention also applies to the process for synthesizing an amido amine as detailed above.

Another aspect of the present invention relates to an amido amine of the following general chemical formula (2), which can be prepared by the process for synthesizing an amido amine from a linear alcohol having from 8 to 22 carbon atoms according to the present invention:

(2)

wherein R is a saturated or unsaturated linear hydrocarbon radical having from 8 to 22 carbon atoms.

Should the disclosure of any patents, patent applications, and publications which are incorporated herein by reference conflict with the description of the present application to the extent that it may render a term unclear, the present description shall take precedence.

Other details or advantages of the present invention will become more clearly apparent through the examples given below. The present invention will be elucidated by the following examples, which are intended to demonstrate, but not to restrict the invention.

EXAMPLES

Examples 1-4: Synthesis of β-Alkoxy Alkyl Esters

Example 1: Synthesis of β-Alkoxy Methyl Ester Through Condensation of Oleyl Alcohol (85%) with Tert-Butyl Acrylate Followed by Transesterification with Methanol (MeOH)

In a 100 mL of round bottom flask equipped with a mechanical stirring, 60 mL of oleyl alcohol (85% Sigma-Aldrich) and subsequently 0.341 g of potassium tert-butoxide (KOtBu) (1.6 mol % with respect to oleyl alcohol) were added. The resulting mixture was allowed to stir at room temperature (r.t.), and 28.4 mL of tert-butyl acrylate (1.02 equivalent with respect to the alcohol) was slowly added to the mixture for 2 hours, while keeping the reaction medium at r.t. After additional 1 hour, another crop of 0.341 g of KOtBu (1.6 mol % with respect to the alcohol) was added and the mixture was allowed to stir at r.t. for additional 2 hours.

When the reaction conversion reached 90%, 250 mL of a $H_2SO_4$/MeOH (0.15 M) solution was slowly added to the reaction medium and the resulting solution was stirred at 60° C. overnight for transesterification to be completed.

The mixture was then neutralized by adding 7 mL of aqueous NaOH (5M) followed by the addition of 500 mL of saturated aqueous NaCl solution. The product was obtained by extraction of 2 times using 500 mL of ether per extraction and the organic phases were combined, dried over MgSO$_4$, filtered and evaporated to afford around 60.3 g of crude product as a pale yellow oil.

The product was further purified by flash chromatography on silica gel using mixture of cyclohexane:diethyl ether (Et$_2$O) (98:2) as an eluent affording finally 46.6 g of pale yellow oil (70% isolated yield).

Figure 1:
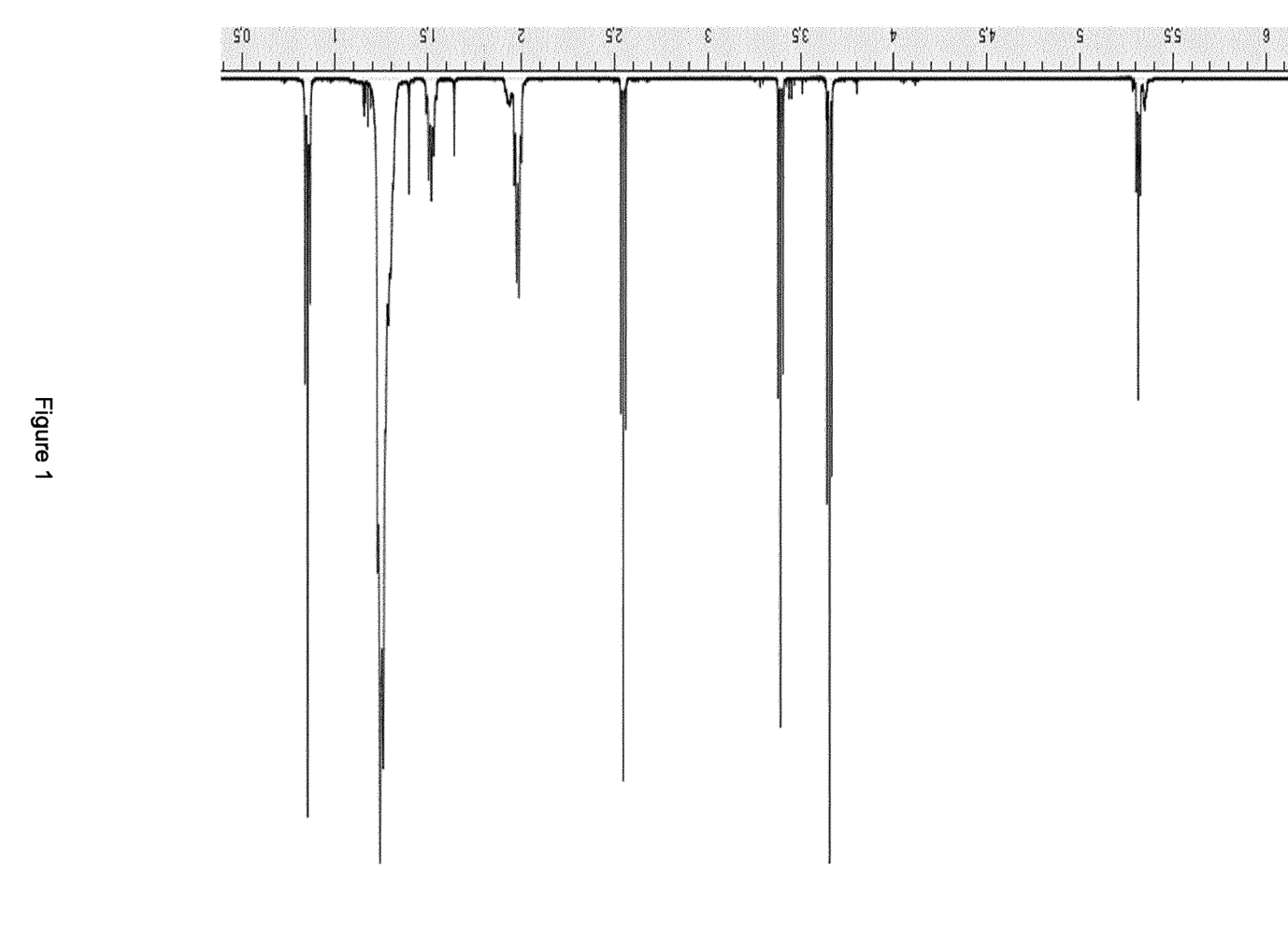
FIG. 1 is $^1$H NMR spectra of the product from Example 1.

$^1$H NMR spectroscopy of the product is provided in FIG. 1.

Example 2: Synthesis of β-Alkoxy Ethyl Ester Through Condensation of Oleyl Alcohol (85%) with Acrylonitrile Followed by a Pinner Reaction In a 100 mL round bottom flask equipped with a condenser and a mechanical stirring, 23.6 mL of oleyl alcohol (85% Sigma-Aldrich) and subsequently 0.264 g (3.2 mol % with respect to the oleyl alcohol) of KOtBu were added. The resulting mixture was heated to 40° C. under stirring and 5.04 mL of acrylonitrile (1.02 equivalent with respect to the fatty alcohol) was slowly added over 4 hours, while keeping the temperature of the reaction medium not to exceed 40° C. The resulting mixture was analyzed by GC/MS (Gas Chromatography Mass Spectrometry) and $^1$H NMR showing that the reaction was very selective and complete. The yield was more than 93% according to NMR analysis.

The mixture was then allowed to cool down to 0° C. and a concentrated H$_2$SO$_4$/ethanol (EtOH) solution, which was previously prepared by diluting 28 mL of sulfuric acid (7 equivalents with respect to the oleyl alcohol) with 100 mL of EtOH at 0° C., was slowly added under stirring into the vessel. The mixture was allowed to continue to stir at 80° C. during 3 days to achieve completion of the Pinner reaction. The mixture was cooled again to 0° C. and 100 mL of an aqueous NaOH (5M) solution was slowly added in order to neutralize the excess of acid so as to adjust pH more than 3 at the end of the addition, followed by addition of 500 mL of H$_2$O. The product was obtained by extraction of three times using 300 mL of ether per extraction and the organic phases were combined, dried over MgSO$_4$, filtered and the solvent was removed under vacuum to afford β-alkoxy ester as pale yellow oil (19.3 g, 70% of isolated yield).

Figure 2:
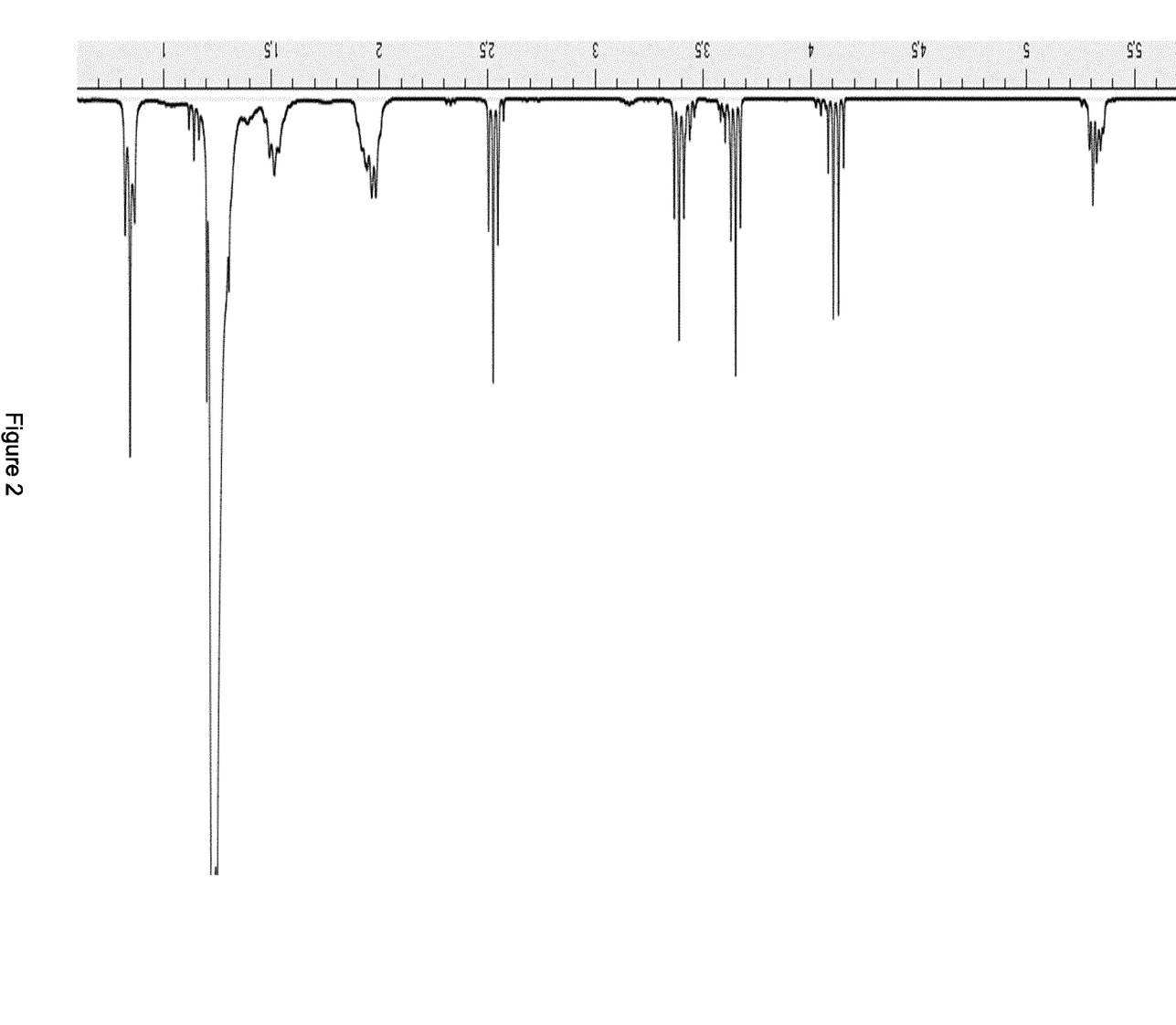
FIG. 2 is $^1$H NMR spectra of the product from Example 2.

$^1$H NMR analysis of the product confirming its structure is provided in FIG. 2.

Example 3: Synthesis of β-Alkoxy Methyl Ester Through Condensation of Oleyl Alcohol (60%) with Tert-Butyl Acrylate Followed by Transesterification with MeOH In a 100 mL round bottom flask equipped with a mechanical stirring, 31 mL of oleyl alcohol (60% Sigma-Aldrich) and subsequently 0.180 g of KOtBu (1.6 mol % with respect to oleyl alcohol) were added. The resulting mixture was allowed to stir at r.t. and 15 mL of tert-butyl acrylate (1.02 equivalents with respect to the alcohol) was slowly added to the mixture for 2 hours, while keeping the reaction medium at r.t. After additional 1 hour, another crop of 0.180 g of KOtBu (1.6 mol % with respect to the alcohol) was added and the mixture was then allowed to stir at r.t. during additional 2 hours.

When the reaction conversion reached 91%, 125 mL of a H$_2$SO$_4$/MeOH (0.15 M) solution was slowly added to the reaction medium and the resulting solution was stirred at 60° C. overnight for transesterification to be completed. The mixture was neutralized by adding 3.5 mL of aqueous NaOH (5 M) followed by the addition of 250 mL of saturated aqueous NaCl solution. The product was obtained by extraction of two times using 250 mL of ether per extraction and the organic phases were combined, dried over MgSO$_4$, filtered and evaporated to afford around 32 g of crude product as a pale yellow oil. The product was further purified by flash chromatography on silica gel using mixture of cyclohexane:Et$_2$O (98:2) as an eluent affording finally 16.3 g of pale yellow oil (46% isolated yield).

Figure 3:
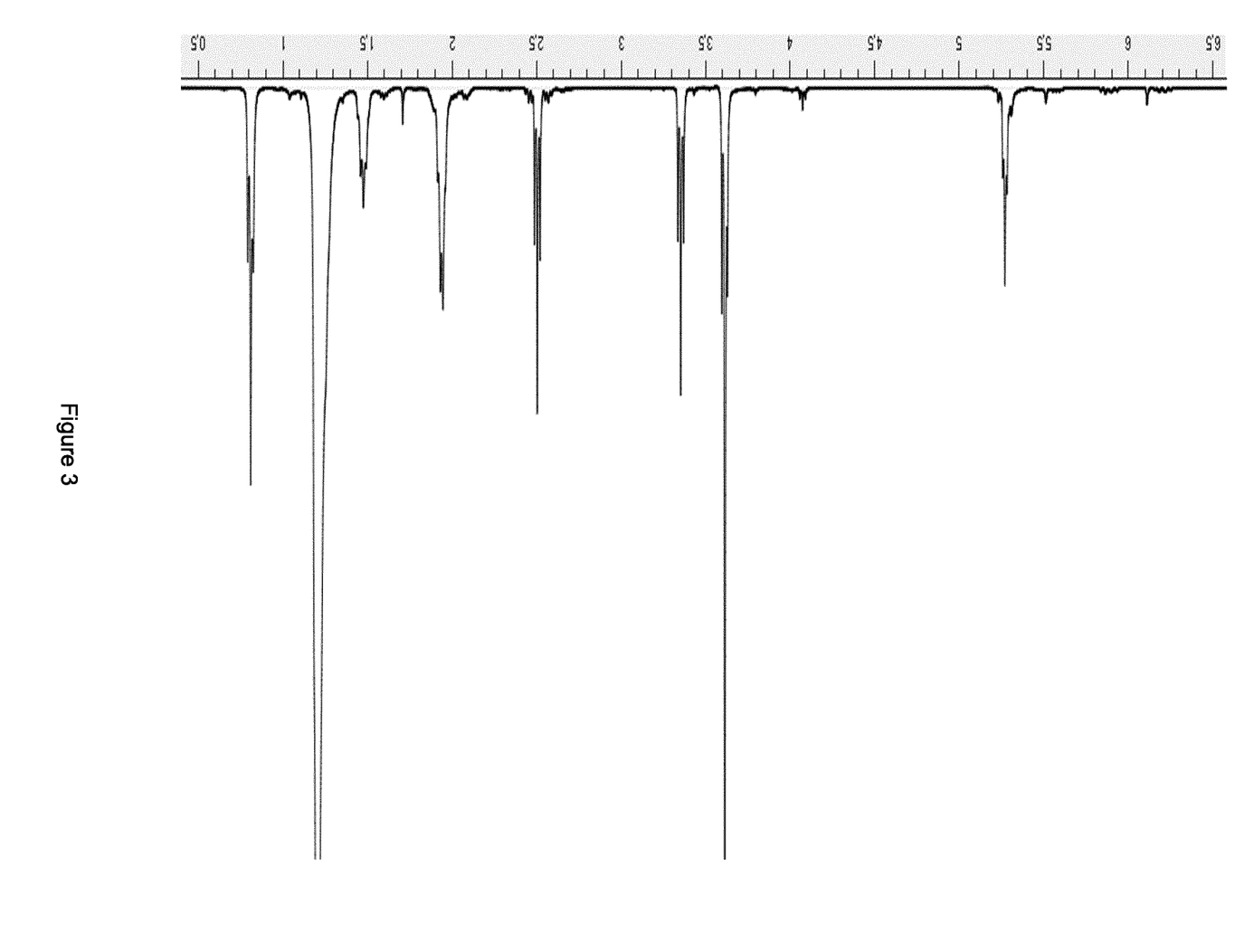
FIG. 3 is $^1$H NMR spectra of the product from Example 3.

$^1$H NMR analysis of the product confirming its structure is provided in FIG. 3.

Example 4: Synthesis of β-Alkoxy Methyl Ester Through Condensation of Erucyl Alcohol (98%) with Tert-Butyl Acrylate Followed by Transesterification with MeOH In a 100 mL round bottom flask equipped with a mechanical stirring, 23.6 mL of erucyl alcohol (98% Sigma-Aldrich) and subsequently 0.111 g of KOtBu (1.6 mol % with respect to erucyl alcohol) were added. The mixture was allowed to stir at 40° C. in order to keep erucyl alcohol melted, and 9.3 mL of tert-butyl acrylate (1.02 equivalents with respect to the alcohol) was slowly added to the mixture for 2 hours, while keeping the reaction medium at 40° C. After additional 1 hour, another crop of 0.111 g of KOtBu (1.6 mol % with respect to the alcohol) was added and the mixture was then allowed to stir at r.t. for additional 2 hours. 0.111 g of KOtBu was added once more (1.6 mol % with respect to erucyl alcohol) and the mixture was then stirred for 1 hour to increase the conversion rate of the starting material.

100 mL of a H$_2$SO$_4$/MeOH (0.15 M) solution was slowly added to the reaction medium and then continued stirring at 60° C. overnight for transesterification to be completed.

The mixture was neutralized by adding 3.5 mL of aqueous NaOH (5 M) followed by the addition of 200 mL of saturated aqueous NaCl solution. The product was obtained by extraction of two times using 200 mL of ether per extraction and the organic phases were combined, dried over MgSO$_4$, filtered and evaporated to afford around 22.3 g of crude product as a pale yellow oil. The product was further purified by flash chromatography on silica gel using mixture of cyclohexane:Et$_2$O (98:2) as an eluent affording finally 15.1 g of pale yellow oil (59% isolated yield).

Figure 4:
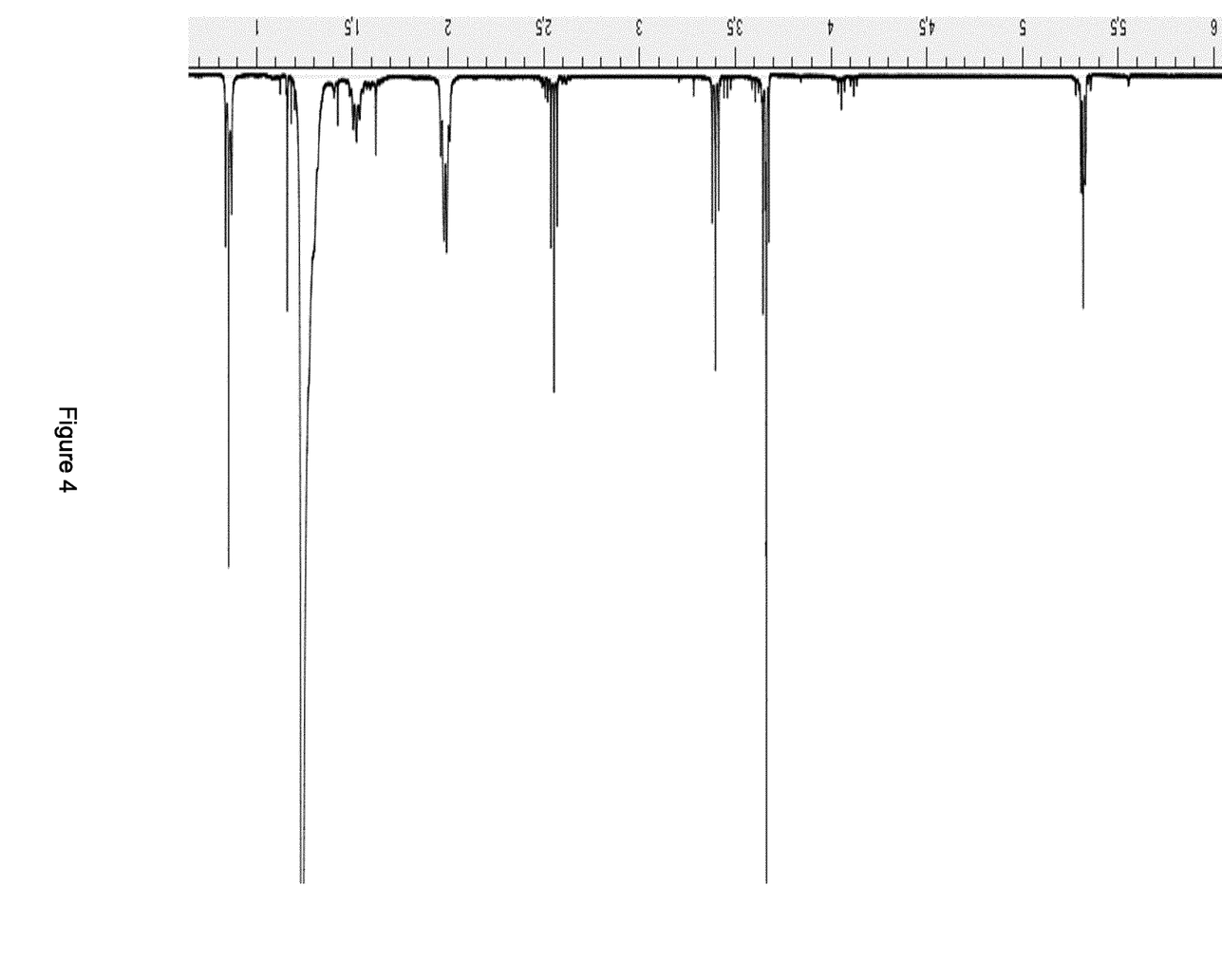
FIG. 4 is $^1$H NMR spectra of the product from Example 4.

$^1$H NMR analysis of the product, that is β-alkoxy ester derived from erucyl alcohol, is provided in FIG. 4.

Examples 5-7: Synthesis of Amido-Amines

Example 5: Synthesis of Amido-Amine from β-Alkoxy Methyl Ester Obtained from Example 1 Using Oleyl Alcohol (85%)

The reaction was carried out under argon atmosphere. In a 250 mL round bottom flask equipped with a distillation apparatus, 46.5 g of β-alkoxy ester obtained from Example 1 and subsequently 17.4 g of dimethylaminopropylamine (DMAPA) was added. Then, 75 µL of MeONa/MeOH (25 wt %) (0.25 mol % with respect to the ester) was added to the mixture and stirring was continued at 140° C. during one day.

Methanol, which was formed during the reaction, was progressively distilled off. The reaction was quenched with 20 mg of acetic acid and the excess of DMAPA was distilled under vacuum. The crude product was purified by flash chromatography on silica gel using CH$_2$CL$_2$ first as an eluent followed by CH$_2$Cl$_2$:MeOH:CH$_3$COOH (90:09:01).

After evaporation, the product was obtained as 23.0 g of pale yellow oil (41% isolated yield).

Figure 5:
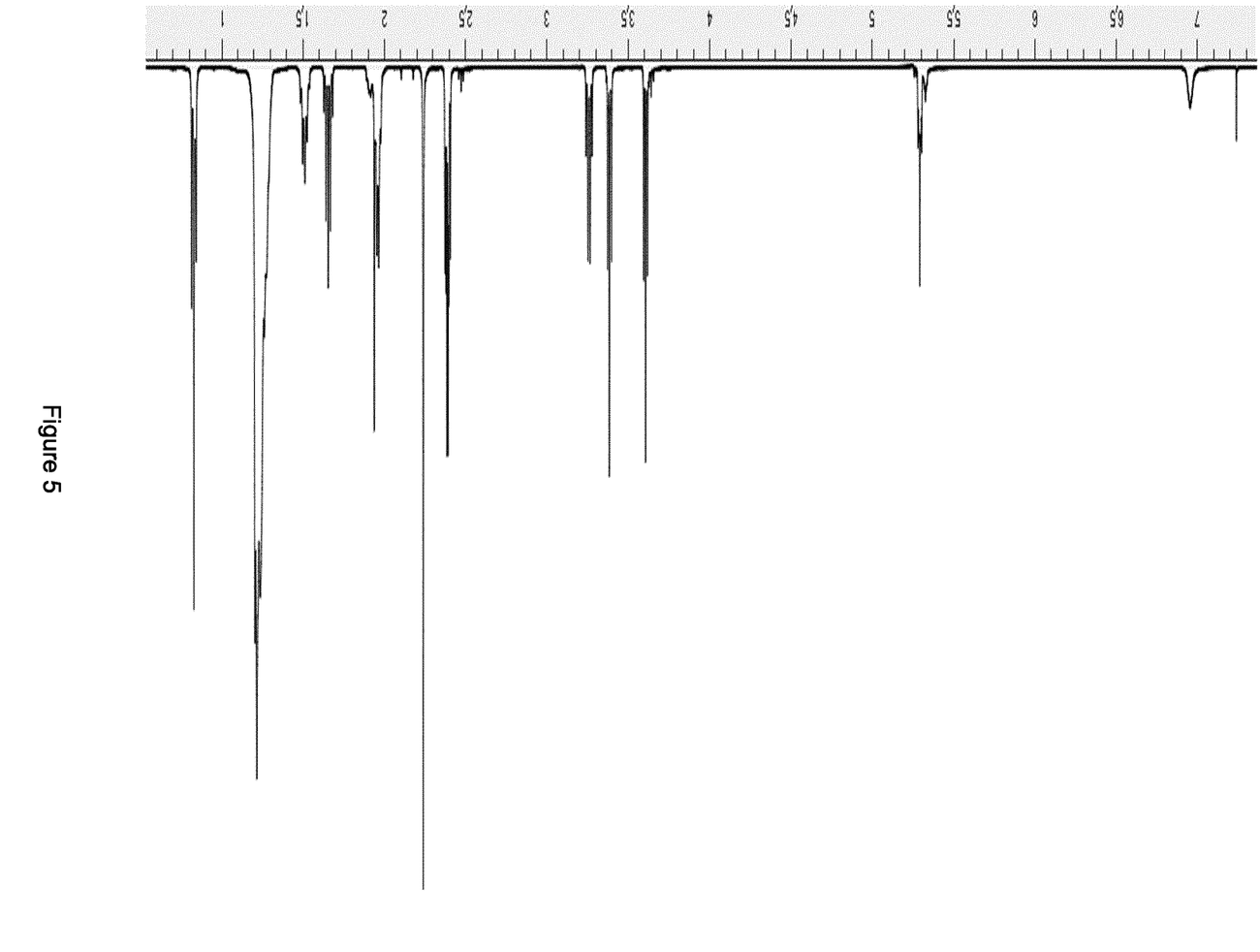
FIG. 5 is $^1$H NMR spectra of the product from Example 5.

$^1$H NMR analysis of the product is provided in FIG. 5.

Example 6: Synthesis of Amido-Amine from β-Alkoxy Methyl Ester Obtained from Example 3 Using Oleyl Alcohol (60%)

Same protocol as Example 5 was followed starting from 16.2 g of β-alkoxy ester. 9.3 g of product was obtained as pale yellow oil (48% isolated yield).

Example 7: Synthesis of Amido-Amine from β-Alkoxy Methyl Ester Obtained from Example 4 Using Erucyl Alcohol (98%)

The reaction was carried out under argon atmosphere. In a 100 mL round bottom flask equipped with a distillation apparatus, 15 g of β-alkoxy ester obtained from Example 4 and subsequently 4.9 g of DMAPA was added. Then, 21 μL of MeONa/MeOH (25 wt %) (0.25 mol % with respect to the ester) was added to the mixture and stirring was continued at 140° C. during one day.

Methanol, which was formed during the reaction, was progressively distilled off. The reaction was quenched with 5 mg of acetic acid and the excess of DMAPA was distilled under vacuum. The crude product was purified by flash chromatography on silica gel using $CH_2CL_2$ first as an eluent followed by $CH_2Cl_2$:MeOH:$CH_3$COOH (80:20:01).

After evaporation, the product was obtained as 6.0 g of pale yellow oil (34% isolated yield).

Figure 6:
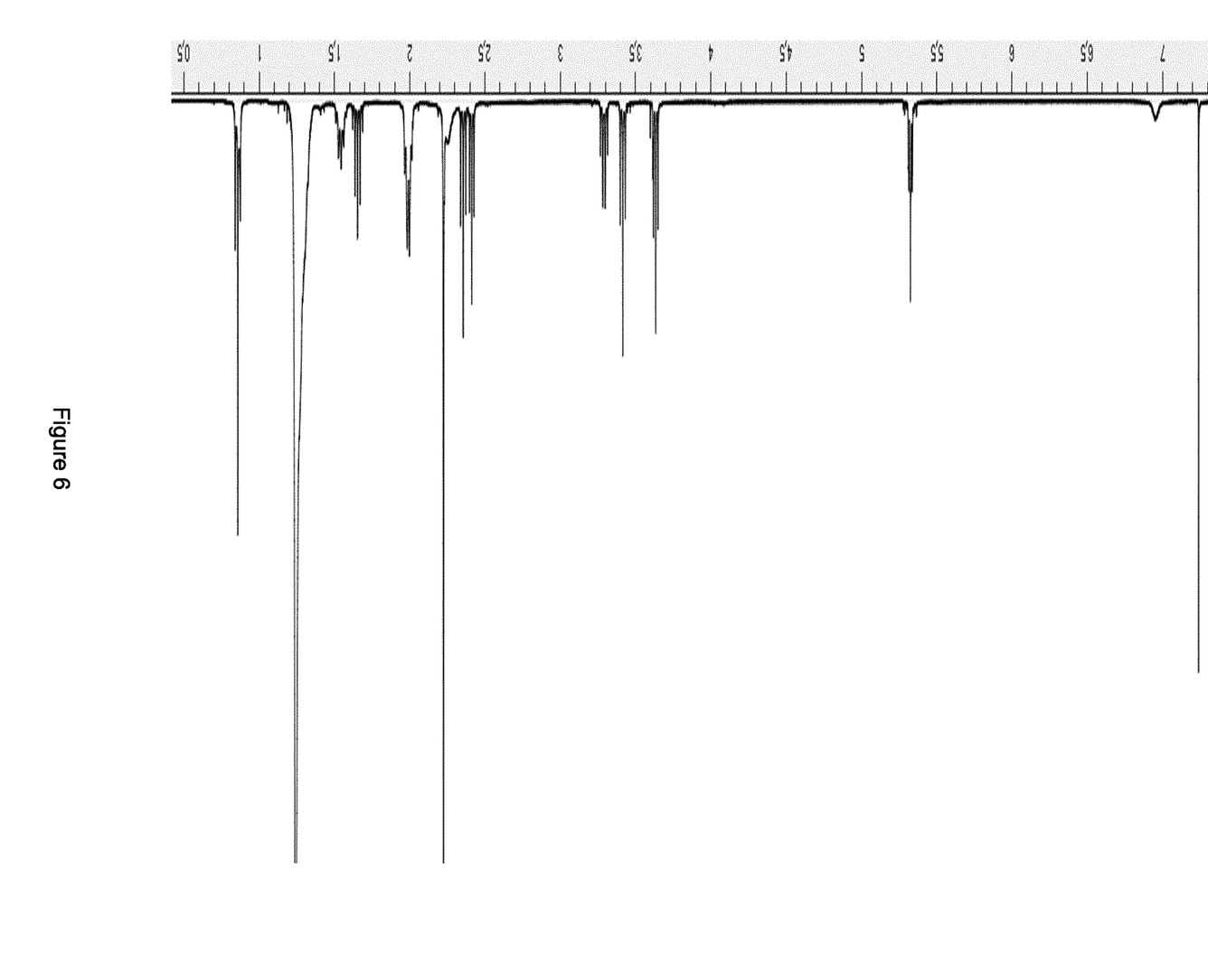
FIG. 6 is $^1$H NMR spectra of the product from Example 7.

$^1$H NMR analysis of the product is provided in FIG. 6.

Examples 8-10: Synthesis of Betaines

Example 8: Synthesis of Betaine from Amido-Amine Obtained from Example 5 Using Oleyl Alcohol (85%)

In a 100 mL round bottom flask equipped with a mechanical stirring, 22.8 g of amido-amine obtained from Example 5 was dissolved in 15 mL of iso-propyl alcohol (i-PrOH) and 18 mL of water. 7 g of SMCA (1.1 equivalents with respect to the amido-amine) was added in one portion to the mixture and stirring was continued at 80° C. until there remains no free amido-amine, which was checked by $^1$H NMR in DMSO-$d_8$. Additional amount of SMCA was added to achieve full conversion of the starting material.

The obtained pale yellow viscous solution (50 wt % in $H_2$O/i-PrOH) was used as such.

Example 9: Synthesis of Betaine from Amido-Amine Obtained from Example 6 Using Oleyl Alcohol (60%)

Same protocol as Example 8 was followed starting from 9.3 g of amido-amine. The product (45 wt % in i-PrOH/$H_2$O) was obtained as a pale yellow viscous solution.

Example 10: Synthesis of Betaine from Amido-Amine Obtained from Example 7 Using Erucyl Alcohol (98%)

In a 100 mL round bottom flask equipped with a mechanical stirring, 5.9 g of amido-amine obtained from Example 7 was dissolved in 2.6 g of i-PrOH and 4.0 g of water. 1.6 g of SMCA (1.1 equivalents with respect to the amido-amine) was added in one portion to the mixture and stirring was continued at 80° C. until there remains no free amido-amine, which was checked by $^1$H NMR in DMSO-$d_8$. Additional amount of SMCA was added to achieve full conversion of the starting material.

The obtained pale yellow viscous solution (45 wt % in $H_2$O/i-PrOH) was used as such.

Comparison of rheological properties of betaines obtained from Examples 8 and 9, and that of commercially available betaine in terms of viscosity: The rheological properties of betaines obtained from Examples 8 and 9 and a commercially available betaine (Mirataine® BET O-30; betaine derived from oleic acid) have been compared by measuring the evolution of viscosity (in centiposie, i.e., in cP) versus the temperature of a 2 wt % KCl brine solution containing the betaine at a concentration around 1.5 wt % (more specifically, 1.3 wt % for Example 8, and 1.5 wt % for Example 9 and Mirataine® BET O-30) and at a shear rate of 100 s$^{-1}$. The viscosity performance of the viscoelastic gels were characterized with a Brookfield® PVS rheometer, using a bob and cup geometry (R1B5). The tests were done under pressure (200 psi) to minimize evaporation at high temperatures as well as to keep the sample from climbing into the shaft. The typical rheological protocol is a constant shear rate of 100 s$^{-1}$, while linearly increasing the temperature. The 100 s$^{-1}$ shear rate corresponds to the average shear rate that the fracturing fluid experiences within a fracture. The viscosity values were calculated from the applied torque and strain using the Brookfield RheoVision Software. In order to ensure accuracy of the results, the Brookfield rheometer was calibrated monthly by using a standard calibration fluid and correcting the torque multiplier accordingly. A typical viscosity-temperature profile for a viscoelastic surfactant at 100 s$^{-1}$ can display peaks and valleys, depending on the surfactant chemistry and concentration. Per customer specification, the performance test on all viscoelastic surfactants in this study was performed at a temperature ramp at a shear rate of 100 s$^{-1}$. The curves are provided in FIG. 7. In contrast, a betaine obtained from Example 10 couldn't be evaluated in the same conditions as the ones obtained from Examples 8 and 9, because of its lower solubility in brine solution, which is probably caused by its longer hydrophobic chain.

Figure 7:
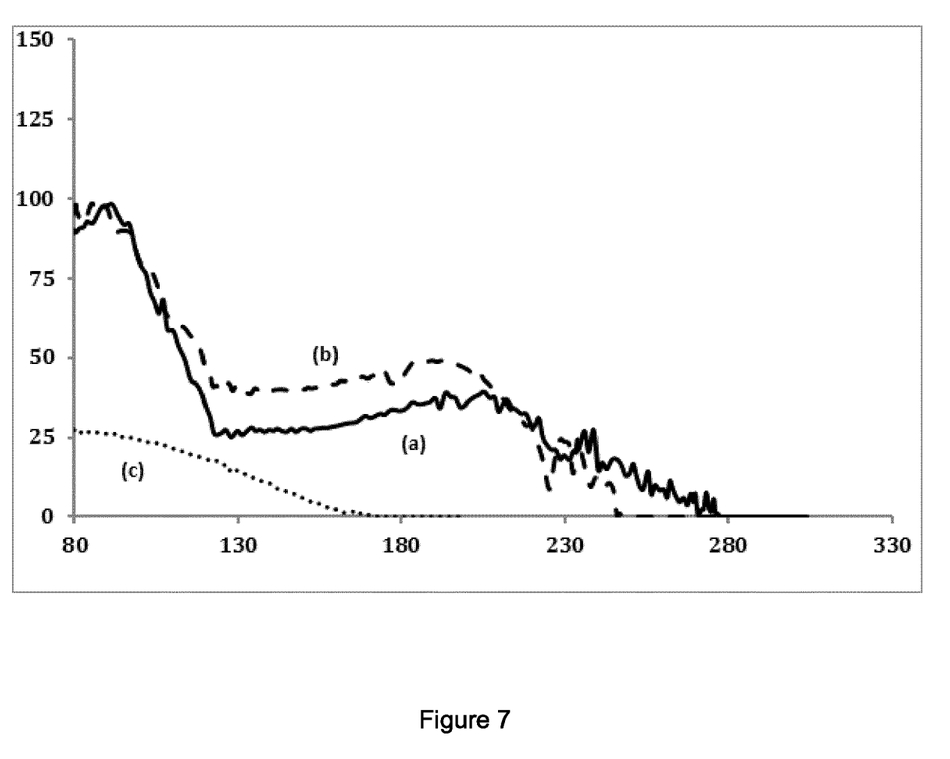
FIG. 7 demonstrates an evolution of viscosity profile as a function of temperature at a shear rate of 100 s$^{-1}$ with regard to the products from Examples 8 and 9, and a commercially available betaine (Mirataine® BET O-30, which is a betaine derived from oleic acid).

As shown in FIG. 7, β-alkoxy betaines derived from oleyl alcohol (Examples 8 and 9) according to the process of the present invention exhibited significantly better rheological properties than the commercially available betaine made from oleic acid (Mirataine® BET O-30). More precisely, FIG. 7 showed similar curves of two betaines made from the same alcohol, i.e., oleyl alcohol, but in different grades (Examples 8 and 9). As demonstrated in FIG. 7, the commercially available betaine made from oleic acid (Mirataine® BET O-30) exhibited very low viscosity in comparison with the betaines obtained from Examples 8 and 9, and its viscosity converged upon zero at around 82° C. (corresponding to about 180° F. as expressed in FIG. 7).

The invention claimed is:
1. A process for synthesizing an amido alkyl betaine from a linear alcohol having from 8 to 22 carbon atoms, the process comprising
   a) in a first step, the linear alcohol having from 8 to 22 carbon atoms is condensed with an acrylonitrile to produce a β-alkoxy nitrile or with an alkyl acrylate to produce a β-alkoxy ester;

b) in a second step, the β-alkoxy nitrile or β-alkoxy ester obtained from step a) is reacted with a short chain alcohol having from 1 to 4 carbon atoms to produce a β-alkoxy alkyl ester;
c) in a third step, said β-alkoxy alkyl ester is reacted with an amino alkyl amine to produce an amido amine; and
d) in a fourth step, said amido amine is reacted with an alkylating agent to produce the amido alkyl betaine.

2. The process according to claim 1, wherein in step a), the acrylonitrile or the alkyl acrylate is added to the linear alcohol having from 8 to 22 carbon atoms for a duration of from 0.5 to 4 hours at a temperature of from 10° C. to 80° C.

3. The process according claim 1, wherein in step a), the acrylonitrile or the alkyl acrylate is added in an equivalent from 0.8 to 2.0 with respect to the linear alcohol having from 8 to 22 carbon atoms.

4. The process according to claim 1, wherein step b) is carried out at a temperature of from 50 to 250° C. for a duration of from 0.5 to 72.0 hours.

5. The process according to claim 1, wherein step c) is carried out at a temperature of from 90 to 150° C. for a duration of from 0.5 to 24.0 hours under an inert atmosphere.

6. The process according to claim 1, wherein the amino alkyl amine in step c) is dimethylaminopropylamine (DMAPA).

7. The process according to claim 1, wherein the alkylating agent in step d) is sodium monochloroacetate (SMCA).

8. The process according to claim 1, wherein step d) is carried out at a temperature of from 60 to 90° C. for a duration of from 0.5 to 24.0 hours under an inert atmosphere.

9. The process according to claim 1, wherein in step d), the alkylating agent is added in an equivalent from 1.0 to 2.0 with respect to the amido amine.

10. The process according to claim 1, wherein the linear alcohol having from 8 to 22 carbon atoms is selected from the group consisting of 1-octanol, 1-decanol, 1-dodecanol, 1-tetradecanol, 1-hexadecanol, 1-octadecanol, oleyl alcohol, 1-icosanol, erucyl alcohol, 1-docosanol, and mixtures thereof.

11. A process for synthesizing an amido amine of the following general chemical formula:

wherein R is a saturated or unsaturated linear hydrocarbon radical having from 8 to 22 carbon atoms, from a linear alcohol having from 8 to 22 carbon atoms, the process comprising
a) in a first step, the linear alcohol having from 8 to 22 carbon atoms is condensed with an acrylonitrile or an alkyl acrylate to produce a β-alkoxy nitrile or a β-alkoxy ester respectively;
b) in a second step, the β-alkoxy nitrile or β-alkoxy ester obtained from step a) is reacted with a short chain alcohol having 1 to 4 carbon atoms to produce a β-alkoxy alkyl ester; and
c) in a third step, said β-alkoxy alkyl ester is reacted with DMAPA to produce the amido amine,
wherein in step a), the acrylonitrile or the alkyl acrylate is added in an equivalent from 0.8 to 2.0 with respect to the linear alcohol having from 8 to 22 carbon atoms.

12. The process according to claim 1, wherein, in step a), the linear alcohol having from 8 to 22 carbon atoms is condensed with an acrylonitrile to produce a β-alkoxy nitrile.

13. The process according to claim 1, wherein, in step a), the linear alcohol having from 8 to 22 carbon atoms is condensed with an alkyl acrylate to produce a β-alkoxy ester.

14. The process according to claim 12, wherein:
in step a), the acrylonitrile is added to the linear alcohol having from 8 to 22 carbon atoms for a duration of from 0.5 to 4 hours at a temperature of from 10° C. to 80° C.,
step b) is carried out at a temperature of from 50 to 250° C. for a duration of from 0.5 to 72.0 hours,
step c) is carried out at a temperature of from 90 to 150° C. for a duration of from 0.5 to 24.0 hours under an inert atmosphere, and
step d) is carried out at a temperature of from 60 to 90° C. for a duration of from 0.5 to 24.0 hours under an inert atmosphere.

15. The process according to claim 13, wherein:
in step a), the alkyl acrylate is added to the linear alcohol having from 8 to 22 carbon atoms for a duration of from 0.5 to 4 hours at a temperature of from 10° C. to 80° C.,
step b) is carried out at a temperature of from 50 to 250° C. for a duration of from 0.5 to 72.0 hours,
step c) is carried out at a temperature of from 90 to 150° C. for a duration of from 0.5 to 24.0 hours under an inert atmosphere, and
step d) is carried out at a temperature of from 60 to 90° C. for a duration of from 0.5 to 24.0 hours under an inert atmosphere.

* * * * *